United States Patent [19]

Thomas

[11] 4,025,499

[45] May 24, 1977

[54] PREPARATION OF HISTIDINE-CONTAINING PEPTIDES

[75] Inventor: Alford Mitchell Thomas, Gurnee, Ill.

[73] Assignee: Abbott Laboratories, North Chicago, Ill.

[22] Filed: Nov. 3, 1975

[21] Appl. No.: 628,164

[52] U.S. Cl. .............. 260/112.5 R; 260/112.5 LH; 260/112.5 TR
[51] Int. Cl.² ....................................... C07C 103/52
[58] Field of Search ........ 260/112.5 TR, 112.5 LH, 260/112.5 R

[56] References Cited

UNITED STATES PATENTS

| | | | |
|---|---|---|---|
| 3,753,969 | 8/1973 | Folkers et al. | 260/112.5 TR |
| 3,757,003 | 9/1973 | Folkers et al. | 260/112.5 TR |
| 3,876,624 | 4/1975 | McGregor | 260/112.5 TR |
| 3,931,138 | 1/1976 | Fujino et al. | 260/112.5 TR |

*Primary Examiner*—Dolph H. Torrence
*Attorney, Agent, or Firm*—Paul D. Burgauer; Robert L. Niblack

[57] ABSTRACT

A process for preparing a peptide with His or 3-Me-His at the C-terminus wherein the coupling with said His or (3-Me) His is carried out in the presence of triethylamine.

5 Claims, No Drawings

PREPARATION OF HISTIDINE-CONTAINING PEPTIDES

DETAILED DESCRIPTION OF THE INVENTION

Peptides carrying a free His or 3-Me-His moiety at the C-terminus are frequently needed in the preparation of physiologically active peptides such as LH-RH, FSH or TRH. In the past, these peptides were always made by coupling His or 3-Me-His to an active ester of the aminoacid or aminoacid chain while said His or 3-Me-His is in the form of a salt, ester or attached to a resin. Routinely, sodium carbonate or bicarbonate is used for this coupling, yielding the corresponding His-Na salt at the C-terminus. In these cases, as well as with esters, the peptide carrying the free acid form of the His moiety at the C-terminus has to be derived from said salt, ester or "resin backing" by a subsequent and separate reaction.

It has now been found that a peptide of the formula

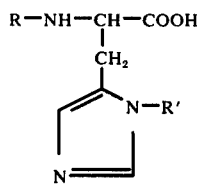

wherein R' is hydrogen or methyl and R represents the acyl moiety of an aminoacid or aminoacid chain which, in turn, carries a blocking group at the N-terminus and wherein any functional groups may be protected by carrying a moiety that can be removed chemically without affecting any of the aminoacid links, can be prepared by a one-step process.

This novel process consists essentially in stirring His or (3-Me) His with one molar equivalent of an active ester of the aminoacid of formula R-OH in the presence of an inert reaction medium and at least one molar equivalent of triethylamine for at least 1 hour at a temperature below 30° C and evaporating said reaction medium.

The above reference to an inert reaction medium is intended to indicate that said medium does not reach with any of the reactants or expected products in the reaction mixture. A preferred medium, commonly used in the aminoacid coupling field is dimethylformamide (DMF), although others such as methylene chloride, chloroform, dimethylacetamide, dioxane, tetrahydrofurane, methyl acetate and the like may be used in its place. The reaction time is not very critical: in about 1 hour, most of the coupling is usually completed, but for convenience, reactions of this type are often continued for longer periods, e.g., overnight. No adverse effect occurs when extended periods are used.

The reaction is preferably carried out at room temperature or at least below 30° C. However, sometimes it is preferred to use temperatures near 0° C, particularly when the aminoacid or aminoacid chain R contains relatively unstable protective and/or N-blocking groups. For the same reason, it is also preferred to use a reaction medium that is easy to remove at reasonably low temperatures without use of unduly reduced pressures. During the evaporation of the medium, any excess triethylamine evaporates with the reaction medium and the triethylamine that temporarily forms the triethylammonium salt of the peptide chain ending with His or 3-Me His cleaves therefrom as well. Thus, instead of forming a stable ester or salt of His or (3-Me) His which requires a subsequent reaction for saponification, the free peptide acid is obtained in situ with the evaporation of the reaction solvent.

In order to illustrate the process of the present invention, reference is made to the following examples which, however, are not intended to limit the scope of the invention in any respect.

EXAMPLE 1

A solution of 4.2 g. of N-benzyloxycarbonyl-pyroglutamic acid norbornene-2,3-dicarboximide in 10 ml. of DMF is added to a stirred solution of 1.55 g. of histidine and 1.4 ml. of triethylamine in 40 ml. of DMF/$H_2O$ (1:1). The mixture is stirred overnight at room temperature and the solution is then evaporated to dryness. The residue is crystallized from 50 ml. methanol/water (1:1) to yield 3.23 g. (81% of theory) of pyroglutamylhistidine. The crystals sinter and foam at 156° C. without giving a clear melt; $[\alpha]_D^{25} = -1°$ (C=1, DMF).

EXAMPLE 2

A solution of 3.62 g. of tert.-butyloxycarbonyl-L-phenylalanine N-hydroxy-succinimide ester in 15 ml. of DMF is added to a solution of 1.55 g. of L-His and 1.4 ml. of triethylamine in 15 ml. of water. The reaction mixture is stirred overnight at room temperature. The reaction mixture is then evaporated under reduced pressure. The residual oil is dissolved in hot ethyl acetate; upon adding hexane, the formed dipeptide crystallizes in yield of 2.1 g. of pure tert.-butyloxycarbonyl-L-phenylalanyl-L-histidine; m.p.:180-2° C with previous sintering; $[\alpha]_D^{24} +13.2°$ (C=1.34, MeOH).

By replacing His with 1.69 g. of 3-methyl-His, the corresponding t-BOC-Phe-(3-Me) His is obtained in similar yield.

EXAMPLE 3

A solution of 2.805 g. of Z-pGlu-ONB (as used in Example 1), 1.23 g. of 3-Me-His and 0.84 ml. of triethylamine in 15 ml. of DMF and 6 ml. of water is stirred at room temperature overnight. Upon evaporation of the mixture under reduced pressure, an oil is obtained. Trituration of this oil with ethyl acetate and crystallization from ethanol yields 1.972 g. of Z-pGlu-(3-Me) His melting at 198°-9° C; $[\alpha]_D^{24} = -2.46°$ (C = 1.08; DMF).

The new method produces good to excellent yields for the coupling step; in most instances, the yields obtained are quite superior to those obtained by older methods for the preparation of peptides having His in the C-terminus position. In all instances, the new method has the highly economical advantage of being a one-step procedure requiring no complicated protection and deprotection reaction for histidine or 3-methyl-histidine.

A further and significant advantage of the new method is that it overcomes the dangers connected with those synthetic methods that employ the alkali metal salt of His. In such salt methods, the free acid can only be obtained upon titrating the obtained peptide salt with an appropriate acid. This requires a second step and must be carried out with great care since any overtitration results in the formation of an imidazole-nitrogen acid addition salt which is difficult to break without adversely affecting other bonds in the aminoacid or peptide chain.

The compounds made by the process of the present invention are primarily used as intermediates. For instance, the compound made by the process of Example 1 is used in the fragment-type synthesis for GnRH or TRH or other hormonally active substances.

I claim:

1. The process of preparing a di- or polypeptide of the formula

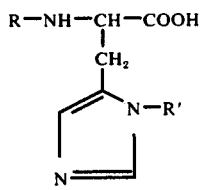

wherein R' is hydrogen or methyl and R represents the acyl moiety of an aminoacid or aminoacid chain which, in turn, carries a blocking group at the N-terminus and wherein any functional groups may be protected by carrying a moiety that can be removed chemically without affecting any of the aminoacid links, consisting essentially in stirring His or (3-Me) His with one molar equivalent of an active ester of the aminoacid of formula R-OH in the presence of an inert reaction medium and at least one molar equivalent of triethylamine for at least 1 hour at a temperature below 30° C and evaporating said reaction medium.

2. The process of claim 1 wherein said R is the acyl moiety of pyroglutamic acid.

3. The process of claim 1 wherein R' is hydrogen.

4. The process of claim 1 wherein R' is methyl.

5. The process of claim 2 wherein R' is hydrogen.

* * * * *